United States Patent [19]
Toth et al.

[11] 3,989,701
[45] Nov. 2, 1976

[54] DIAMINE-BENZOPHENONES AND A PROCESS FOR THE PREPARATION THEREOF

[75] Inventors: Edit Toth; Jozsef Torley; Eva Palosi; Szaboles Szeberenyi; Laszlo Szporny; Sandor Gorog; Csilla Meszaros, all of Budapest, Hungary

[73] Assignee: Richter Gedeon Vegyeszeti Gyar Rt., Budapest, Hungary

[22] Filed: July 3, 1974

[21] Appl. No.: 485,744

[30] Foreign Application Priority Data
July 26, 1973 Hungary.............................. RI 518

[52] U.S. Cl. .................... 260/247.2 A; 260/239 B; 260/239 BE; 260/247.5 R; 260/268 PH; 260/293.78; 260/293.8; 260/307 D; 260/309; 260/309.2; 260/326.13 R; 260/326.16; 260/326.2; 260/326.5 J; 260/570 AB; 424/244; 424/248; 424/210; 424/256; 424/269; 424/330
[51] Int. Cl.²...................................... C07D 295/00
[58] Field of Search............. 260/247.2 A, 247.5 R, 260/376.5 J, 268 PH, 293.78

[56] References Cited
OTHER PUBLICATIONS
R. A. Abramovitch, et al., J. Chem. Soc., 1957, pp. 1781–1788.

Primary Examiner—Paul J. Killos
Attorney, Agent, or Firm—Karl F. Ross; Herbert Dubno

[57] ABSTRACT
New compounds of the general formula (I)

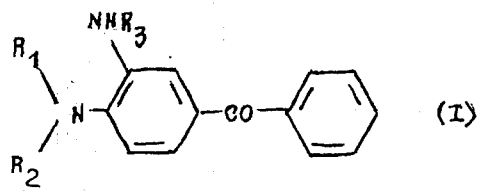

wherein
$R_1$ and $R_2$ each is a saturated or unsaturated, straight-chained or branched alkyl group, an aralkyl group, a saturated or unsaturated cycloalkyl group or an aryl group, or
$R_1$ and $R_2$ together with the adjacent nitrogen atom may form substituted or unsubstituted heterocyclic group with or without a further oxygen or nitrogen heteroatom, and
$R_3$ is hydrogen or an acyl group derived from a $C_{1-18}$ carboxylic acid.

The compounds are prepared by reducing the corresponding nitro compounds of the general formula (II)

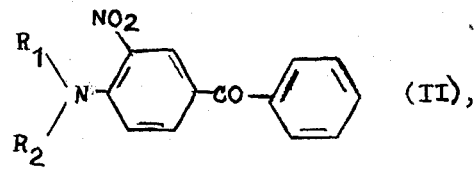

and optionally acylating the obtained product.

The compounds of the general formula (I) and their acid addition salts and quaternary ammonium salts are active primarily in the induction of liver microsomal enzyme, but they also possess valuable antipyretic activity and a yohimbine lethality increasing effect characteristic of antidepressants.

8 Claims, No Drawings

DIAMINE-BENZOPHENONES AND A PROCESS FOR THE PREPARATION THEREOF

This invention relates to new diamino-benzophenones of pharmaceutical activity, to physiologically acceptable acid addition salts and quaternary ammonium salts thereof, and furthermore to a process for the preparation of such compounds.

The compounds according to the invention correspond to the formula (I)

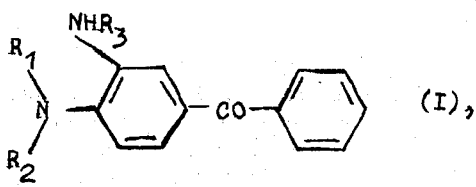

wherein
- $R_1$ and $R_2$ each is a saturated or unsaturated, straight-chained or branched alkyl group, an aralkyl group, a saturated or unsaturated cycloalkyl group or an aryl group, or
- $R_1$ and $R_2$ together with the adjacent nitrogen atom form substituted or unsubstituted heterocyclic group with or without a further oxygen or nitrogen hetero atom, and
- $R_3$ respectively hydrogen or an acyl group derived from a $C_{1-18}$ carboxylic acid.

$R_1$ and $R_2$ can be a saturated or unsaturated, straight-chained or branched $C_{1-18}$ alkyl group (e.g. an alkyl, alkenyl, alkynyl or alkadienyl group), preferably a $C_{1-10}$ group, such as methyl, ethyl, propyl, allyl, butyl, isobutyl, pentyl, isopentyl, hexyl, 1-octen-7-yl, nonyl or decyl group. The aralkyl group is preferably an aryl-$C_{1-4}$ alkyl, more preferably phenyl-$C_{1-4}$ alkyl, e.g. benzyl, phenethyl, 1-naphthyl-ethyl or 3-phenyl-propyl. The saturated or unsaturated cycloalkyl may be, for example, cycloalkyl, cycloalkenyl, cycloalkynyl or cycloalkadienyl, preferably a $C_{3-8}$ monocarbocycle, such as cyclopropyl, cyclopentyl, cyclohexyl, cyclohexenyl, cycloheptyl etc. The aryl is preferably a phenyl or substituted phenyl of the formula $C_6H_4X$, wherein X is halogen (e.g. fluorine, chlorine, bromine or iodine), alkyl as listed above, e.g. methyl, ethyl, hexyl or decyl, alkoxy, e.g. methoxy, ethoxy, propoxy, butoxy, isobutoxy or decyloxy, or the like.

$R_1$ and $R_2$ may form together a saturated or unsaturated alkylene group containing preferably 4 to 10, more preferably 4 to 7 carbon atoms, which, together with the adjacent nitrogen atom, form a heterocyclic group, such as a pyrrolo, pyrrolidino, piperidino, azepino or heptamethyleneimino. Alternatively, $R_1$ and $R_2$ may form together a nitrogen- or oxygen-containing saturated or unsaturated alkylene group, which, together with the adjacent nitrogen atom, may form a heterocyclic group containing more than one hetero atoms, such as a morpholino, imidazolo, indolo, benzimidazolo or 1,4-benzisoxazolo group. These heterocyclic groups may be saturated or unsaturated and may have a substituent, preferably an alkyl group, on either of the atoms constituting the ring.

$R_3$ may represent, as an acyl group derived from a $C_{1-18}$ carboxylic acid, e.g. formyl, acetyl, propionyl, butynyl, isobutynyl, valeryl, caproyl, pivaloyl, or palmitoyl group, or an acyl group derived from an unsaturated aliphatic carboxylic acid, e.g. acryloyl, propiolyl, methacryloyl, crotonoyl, etc. group, or an acyl group derived from a carbocyclic carboxylic acid, e.g. toluoyl or benzoyl group. These acyl groups may be optionally substituted with a halogen, an alkyl group as defined above, an alkoxy group, etc.

The compounds of the general formula (I) and their salts possess valuable pharmacological properties. According to our experiments these compounds are active primarily in the induction of liver microsomal enzymes, but they also possess valuable antipyretic activity and a yohimbine lethality increasing effect characteristic of anti-depressant activity. As reference substances, phenobarbital, phenacetine and imipramine [5-(3-dimethylaminopropyl)-10,11-dihydro-5H-dibenz(b,f)azepin] were used in the experiments.

The pharmacological tests were carried out as follows:

To investigate the enzyme inductive effect, Wistar female rats, each weighing 40 to 50 g. were treated with pure solvent, or with a dosage of 60 mg./kg. of phenobarbital or the compound to be tested, respectively. 24 hours after this treatment 40 mg./kg. of hexobarbital were administered intravenously into the animals. The decrease of the elimination period and the liver enzyme induction was expressed as the shortening of duration of sleeping. The results of these tests are given in Table 1.

To test the antipyretic effect, a 15% yeast suspension was administered to male rats each weighing 180 ±10 g. No food was given to the animals, they could consume, however, arbitrary amount of water. 16 hours after the administration of yeast the rectal temperature of the animals was taken, and the animals were treated with pyragro in an intravenous dosage of 50 M bact./animal. The compound to be tested was administered orally into the animals, thereafter the change in rectal temperature both for the treated and the control animals was recorded for 5 hours, using an "Elab" type electrothermometer. Phenacetine, used as reference substance, and the compounds of the invention were administered in dosages of 40 mg./kg. body weight. The results of this test are listed in Table 2.

To investigate the yohimbine-potentiating effect, CFLP male mice each weighing 20 to 25 g. were treated orally with the compounds according to the invention, and 1 hour after this treatment yohimbine was injected subcutaneously into the animals in a dosage of 20 mg./kg. 24 hours after the introduction of yohimbine the perished animals were counted, and the yohimbine potentiating effect ($ED_{50}$) of the compounds was calculated from these data by probit analysis. As reference substance, imipramine was used. The results of this test are given in Table 3.

In Tables 1 to 3 the following abbreviations are used:
- $C_3$ = 3-amino-4-(N-methyl-piperazino)-benzophenone
- $C_6$ = 3-amino-4-(N-ethyl-N-phenylamino)-benzophenone $C_7$ = 3-amino-4-(N,N-diisobutylamino)-benzophenone
$C_8$ = 3-amino-4-morpholino-benzophenone
$C_{11}$ = 3-propionylamino-4-morpholino-benzophenone HCl
$C_{12}$ = 3-palmitoylamino-4-morpholino-benzophenone
p.o. = per os
S.E. = standard error.

Table 1

| Compound | Inductive effect | |
|---|---|---|
| | Dosage mg./kg. p.o. | Average duration of sleeping ± S.E., minutes |
| Control | — | 27.4 ± 3.02 |
| Phenobarbital | 60 | 5.4 ± 1.63 |
| $C_6$ | 60 | 11.6 ± 2.71 |
| $C_7$ | 60 | 10.0 ± 1.92 |
| $C_{11}$ | 60 | 9.0 ± 1.30 |
| $C_{12}$ | 60 | 10.4 ± 1.02 |

Table 2

| Compound | Antipyretic activity | |
|---|---|---|
| | Dosage mg./kg. | Decrease of temperature °C |
| Phenacetine | 40 | −1.0 |
| $C_8$ | 40 | −1.0 |

Table 3

| Compound | Potentiation of yohimbine lethality |
|---|---|
| | $ED_{50}$ mg./kg. p.o. |
| Imipramine | 9.0 |
| $C_3$ | 30.0 |

Inductive effect: $LD_{50}$ mg./kg. p.o.:
phenobarbital: 240.0; $C_6$: above 400; $C_7$: above 600; $C_{11}$: above 450; $C_{12}$: above 500.
Antipyretic activity: $LD_{50}$ mg./kg. p.o.:
phenacetine: 2405; $C_8$: above 3000.
Potentiation of yohimbine lethality: $LD_{50}$ mg./kg. p.o.:
imipramine: 666; $C_3$: above 3000.

As it appears from the above data, the compounds tested possess valuable activities in three fields, namely as microsomal enzyme inducers, antipyretics and antidepressants. The activities of these compounds are marked and extremely selective.

Thus, for example, compound $C_{11}$ has an enzyme-inducing effect, the same in strength as for phenobarbital, but has no effect on the central nervous system, hence it can be used more advantageously than phenobarbital.

Compound $C_8$ is similar in antipyretic activity to phenacetine, but the former has no harmful effects on the kidneys.

Although compound $C_3$ is inferior in antidepressant activity to imipramine, it can be used to advantage in the therapy, since, unlike imipramine, in the active dosage it causes no ataxis or reflex retardation. ($ED_{50\text{-}rotarod}$: imipramine: 28.0 mg./kg., $C_3$: 160 mg./kg.)

Besides their pharmacological value, the new compounds of the invention can also be used as intermediates in the syntheses of pharmacologically active substances.

The compounds of the formula (I), wherein $R_1$, $R_2$ and $R_3$ each have the same meanings as defined above, can be prepared according to the invention by reducing a compound of the formula (II)

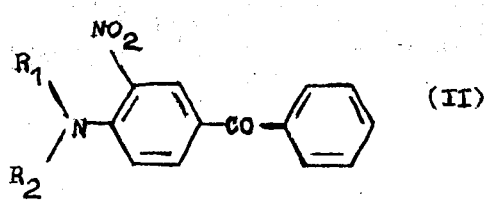

(II)

wherein $R_1$ and $R_2$ are as defined above, and, if desired, acylating the obtained substance with a $C_{1-18}$ carboxylic acid or a reactive derivative thereof. If desired, the thus-obtained free bases are converted into their acid addition salts or quaternary ammonium salts, or the free bases are liberated from the compounds obtained in the form of their acid addition salts.

As described above, the compounds of the formula (I) are prepared by the selective reduction of the compounds of the formula (II) into the corresponding 3-amino-derivatives, and, if desired, by the acylation of the 3-amino group. In this selective reduction only the nitro group in position 3 is converted into an amino group, with the other parts of the molecule remaining unchanged. The reduction can be carried out by various methods, one of them being the hydrogenation of the compounds of the formula (II) with a calculated amount of hydrogen in the presence of a catalyst promoting the reduction of the nitro group. As the catalyst Raney-nickel, platinum or palladium can be used; these latter substances are applied in supported or unsupported form, deposited for instance on activated carbon, an alkaline earth metal carbonate or sulphate, etc.

The reaction is carried out preferably in the presence of an organic solvent, such as benzene, ethanol, tetrahydrofuran or ethyl acetate. The temperature of the reaction is preferably 20° to 50° C.

The reduction can be carried out under atmospheric or higher pressure; the pressure applied is preferably lower than 5 at.

When the reaction has been terminated the catalyst is removed by filtration, and the product is isolated from the filtrate.

The selective reduction can also be carried out by means of a hydrogen donor substance, such as cyclohexene. According to this method a compound of the formula (II) is dissolved in cyclohexene or in a mixture of cyclohexene and another solvent, such as tetrahydrofuran, and the reaction mixture is refluxed in the presence of a metal catalyst such as Raney nickel or metallic palladium. During this reaction cyclohexene is converted into benzene through the formation of 1,3-cyclohexadiene, and the nitro group is reduced simultaneously into an amino group.

The selective reduction of the compounds of the formula (II) can also be carried out by metals ranging in normal electrode potential from −2.04 to +0.05 V, in the presence of an organic or mineral acid, such as hydrochloric acid or glacial acetic acid, or in some instances in the presence of a base, such as sodium hydroxide.

According to a further method of the invention nascent hydrogen liberated from an alkali metal borohydride, such as sodium borohydride is used for the reduction instead of molecular hydrogen. This reaction is conducted optionally in the presence of a catalyst. According to this reduction method first a platinum, palladium or rhodium salt is reacted with sodium borohydride in the presence of a carbon support in ethanol medium. This process yields a very active catalyst. Then hydrochloric acid and the ethanol solution of the compound of the formula (II) is added to the thus-obtained mixture, and finally the ethanol solution of the stoichiometric amount of sodium borohydride is added dropwise. By the nascent hydrogen liberated from sodium borohydride when contacted with hydrochloric acid, the nitro compound is reduced in some minutes.

The acid amides can be prepared by reacting the compounds containing a primary amino group with a $C_{1-18}$ carboxylic acid or a reactive derivative thereof, preferably an acid halide or anhydride. The acylation can be carried out in an inert organic solvent, such as acetone or dioxane, at a temperature ranging from $-10°$ C to the boiling point of the solvent, preferably at 20° to 50° C. Inorganic bases or tertiary organic bases can be used to bind the acid liberated in the reaction, the acid binding agent may be, however, the starting benzophenone derivative itself as it contains primary and tertiary amino groups. This reaction leads directly to the salt of a benzophenone of the formula (I), with an acyl group as substituent $R_3$.

The free bases of the formula (I) can be converted into their acid addition salts by reacting them with organic or mineral acids, e.g. hydrochloric acid, hydrobromic acid, sulphuric acid, phosphoric acid, lactic acid, citric acid, tartaric acid, maleic acid or fumaric acid. The free bases can also be converted into the corresponding quaternary ammonium compounds formed with saturated or unsaturated lower alkyl halides, alkyl sulphates, or benzyl halides.

The bases can be liberated from the acid addition salts and quaternary ammonium compounds according to known procedures. The thus-obtained free bases can be, in turn, converted into other acid addition salts or quaternary ammonium derivatives.

The compounds of the formula (II), used as starting substances, can be prepared e.g. by reacting a 3-nitro-4-halo-benzophenone with a secondary amine of the formula (III)

$R_1 - NH - R_2$        (III)

wherein $R_1$ and $R_2$ each have the same meanings as defined above.

The compounds according to the invention can be administered to the patients in pharmaceutically active but non-toxic dosages. The actual amount of the active agent to be administered depends on the pharmaceutical effect to be attained, moreover on the method of treatment, as well as on the general condition and sensitivity of the patient to be treated.

The effective dosage can be administered either in subdivided form several times a day, or in time-release form.

The pharmacologically active compounds of the invention can be used in the therapy in the form of pharmaceutical compositions. Such compositions suitable for enteral, parenteral or topical administration may contain the new compounds according to the invention in admixture with solid or liquid, organic or inorganic, pharmaceutically acceptable carriers which do not react with the active agents. These carriers include e.g. water, alcohols, gelatine, propylene glycol, vegetable oils, cholesterol, starch, lactose, talc, gum, magnesium stearate, etc. If desired, the pharmaceutical products can be sterilized.

The pharmaceutical compositions may contain auxiliary agents, such as preserving, stabilizing, wetting or emulsifying agents, solubilizing substances, salts or buffers to modify the osmotic pressure, etc. These compositions may contain the compounds of the formula (I) in combination with other therapeutically active agents.

The pharmaceutical compositions are prepared by methods well known in the art. Thus, for example, the injectable compositions are prepared by dissolving an acid addition salt or quaternary ammonium salt of the active agent in pyrogen-free physiological saline solution or in bidistilled water, optionally sterilizing the solution, and filling into ampoules under sterile conditions.

The invention is elucidated in detail by the following non-limiting Examples.

EXAMPLE 1

3-Amino-4-(N,N-diisobutylamino)-benzophenone 10.63 g. of 3-nitro-4-(N,N-diisobutylamino)-benzophenone are dissolved in 106 ml. of ethyl acetate, the solution is poured into a hydrogenating apparatus, and 5,3 g. of Raney-nickel are added. The reaction mixture is hydrogenated at room temperature and atmospheric pressure until the uptake of the calculated amount of hydrogen (this requires generally about 1.5 hours). Thereafter the catalyst is removed by filtration and the clear solution is evaporated to dryness under reduced pressure. The obtained 9.4 g. of solid are recrystallized from isopropanol, to yield pure 3-amino-4-(N,N-diisobutylamino)-benzophenone; m.p.: 59°–60° C.

| Analysis for $C_{21}H_{28}N_2O$: | | |
|---|---|---|
| Calculated: C 77.73 % | H 8.70 % | N 8.63 % |
| Found: C 77.68 % | H 8.55 % | N 8.70 % |

I.R. spectrum: characteristic bands appear at 705, 725, 795, 855, 1650, 2820, 2880, 2940, 2960, 3380, and 3480 $cm^{-1}$.

U.V. spectrum: $\lambda_{max.}^{EtOH}$ 251, 314, 368 nm.

EXAMPLE 2

3-Amino-4-(N,N-di-n-amylamino)-benzophenone 5.72 g. of 3-nitro-4-(N,N-di-n-amylamino)-benzophenone are reduced as described in Example 1 to yield 5.1 g. of 3-amino-4-(N,N-di-n-amylamino)-benzophenone in the form of a viscous, oily product.

| Analysis for $C_{23}H_{32}N_2O$: | | |
|---|---|---|
| Calculated: C 78.36 % | H 9.15 % | N 7.95 % |
| Found: C 78.41 % | H 9.25 % | N 7.78 % |

I.R. spectrum: characteristic bands appear at 715, 730, 795, 855, 1655, 2820, 2860, 2940, 2960, 3360, and 3450 cm$^{-1}$.

U.V. spectrum: $\lambda_{max.}^{EtOH}$ 223, 251, 314, 366 nm.

EXAMPLE 3

3-Amino-4-(N-ethyl-N-cyclohexylamino)-benzophenone 7.1 g. of 3-nitro-4-(N-ethyl-N-cyclohexylamino)-benzophenone are dissolved in a 1:1 mixture of benzene and ethyl acetate, and 0.7 g. of palladiumized carbon are added to the mixture. The mixture is hydrogenated at room temperature and 3 atm. hydrogen pressure until the uptake of the calculated amount of hydrogen (this requires about one hour). Thereafter the catalyst is removed by filtration, and the filtrate is evaporated to dryness under reduced pressure. 6.35 g. of crude product are obtained. After recrystallization from isopropanol, 5.8 g. of pure 3-amino-4-(N-ethyl-N-cyclohexylamino)-benzophenone, melting at 106.5°–107.5° C are obtained.

| Analysis for $C_{21}H_{26}N_2O$: | | | |
|---|---|---|---|
| Calculated: | C 78.22 % | H 8.13 % | N 8.69 % |
| Found: | C 78.31 % | H 8.13 % | N 8.62 % |

I.R. spectrum: characteristic bands appear at 710, 730, 880, 1645, 2860, 2940, 3370, and 3460 cm$^{-1}$.

U.V. spectrum: $\lambda_{max.}^{EtOH}$ 224, 252, 326, 367 nm.

This compound can also be prepared according to the method described in Example 1.

EXAMPLE 4

3-Amino-4-(N-methyl-N-octylamino)-benzophenone 7.36 g. of 3-nitro-4-(N-methyl-N-octylamino)-benzophenone are reduced as described in Example 1 to yield 6.1 g. of 3-amino-4-(N-methyl-N-octylamino)-benzophenone.

| Analysis for $C_{22}H_{30}N_2O$: | | | |
|---|---|---|---|
| Calculated: | C 78.06 % | H 8.93 % | N 8.28 % |
| Found: | C 78.00 % | H 8.77 % | N 8.13 % |

I.R. spectrum: characteristic bands appear at 700, 720, 800, 880, 1650, 2805, 2860, 2940, 2960, 3360, and 3440 cm$^{-1}$.

U.V. spectrum: $\lambda_{max.}^{EtOH}$ 222, 252, 310, 365 nm.

EXAMPLE 5

3-Amino-4-(N-ethyl-N-phenylamino)-benzophenone 10.39 g. of 3-nitro-4-(N-ethyl-N-phenylamino)-benzophenone are reduced as described in Examples 1 or 2, and the obtained 9.4 g. of crude product are recrystallized from isopropanol. 8.5 g. of 3-amino-4-(N-ethyl-N-phenyl-amino)-benzophenone are obtained; m.p.: 82°–82,5° C.

| Analysis for $C_{21}H_{20}N_2O$: | | | |
|---|---|---|---|
| Calculated: | C 79.71 % | H 6.37 % | N 8.85 % |
| Found: | C 79.88 % | H 6.40 % | N 8.93 % |

I.R. spectrum: characteristic bands appear at 695, 735, 740, 750, 795, 850, 1650, 2880, 2940, 2980, 3390, and 3500 cm$^{-1}$.

U.V. spectrum: $\lambda_{max.}^{EtOH}$ 252, 374, 310 nm.

EXAMPLE 6

3-Amino-4-(N-methyl-N-benzylamino)-benzophenone 15.6 g. of 3-nitro-4-(N-methyl-N-benzylamino)-benzophenone are reduced as described in Examples 1 or 2, and the obtained crude solid is recrystallized from methanol. 12.1 g. of 3-amino-4-(N-methyl-N-benzylamino)-benzophenone are obtained, m.p.: 93°–94° C.

| Analysis for $C_{21}H_{20}N_2O$: | | | |
|---|---|---|---|
| Calculated: | C 79.71 % | H 6.38 % | N 8.85 % |
| Found: | C 79.58 % | H 6.51 % | N 8.72 % |

I.R. spectrum characteristic bands appear at 700, 705, 730, 735, 795, 850, 1645, 2800, 2840, 2860, 2960, 3360, and 3940 cm$^{-1}$.

U.V. spectrum: $\lambda_{max.}^{EtOH}$ 214, 252, 306, 364 nm.

EXAMPLE 7

3-Amino-4-morpholino-benzophenone hydrochloride

A solution of 9.37 g. of 3-nitro-4-morpholinobenzophenone in 196 ml. of ethyl acetate is reduced as described in Examples 1 or 2. 8.26 g. of 3-amino-4-morpholinobenzophenone are obtained; m.p.: 138° C.

| Analysis for $C_{17}H_{18}N_2O_2$: | | | |
|---|---|---|---|
| Calculated: | C 72.32 % | H 6.43 % | N 9.92 % |
| Found: | C 72.40 % | H 6.37 % | N 9.85 % |

I.R. spectrum: characteristic bands appear at 705, 725, 800, 880, 1640, 2840, 2860, 2960, 2980, 3320, and 3400 cm$^{-1}$.

U.V. spectrum: $\lambda_{max.}^{EtOH}$ 216, 252, 298, 358 nm.

The methanol solution of the free base is treated with hydrochloric acid dissolved in isopropanol to yield 3-amino-4-morpholino-benzophenone hydrochloride; m.p.: 193°–194° C.

EXAMPLE 8

3-Amino-4-heptamethyleneimino-benzophenone 10.2 g. of 3-nitro-4-heptamethyleneimino-benzophenone are reduced as described in Examples 1 or 2, and the crude product is crystallized from ethanol. 7.8 g. of 3-amino-4-heptamethyleneimino-benzophenone are obtained; m.p.: 85° C.

| Analysis for $C_{20}H_{24}N_2O$: | | | |
|---|---|---|---|
| Calculated: | C 77.88 % | H 7.84 % | N 9.08 % |
| Found: | C 77.78 % | H 7.96 % | N 9.00 % |

I.R. spectrum characteristic bands appear at 700, 730, 800, 890, 1645, 2860, 2930, 3360, and 3430 cm$^{-1}$.

U.V. spectrum: $\lambda_{max.}^{EtOH}$ 221, 251, 318, 370 nm.

EXAMPLE 9

3-Amino-4-pyrrolidino-benzophenone 8.9 g. of 3-nitro-4-pyrrolidino-benzophenone are reduced as described in Examples 1 or 2, and the obtained crude product is crystallized from a mixture of isopropanol and ligroin. 6.9 g. of 3-amino-4-pyrrolidino-benzophenone are obtained; m.p.: 112° C.

| Analysis for $C_{17}H_{18}N_2O$: | | |
|---|---|---|
| Calculated: C 76.66 % | H 6.81 % | N 10.52 % |
| Found: C 76.70 % | H 6.81 % | N 10.43 % |

I.R. spectrum: characteristic bands appear at 710, 745, 795, 875, 1640, 2840, 2880, 2960, 2980, 3340, and 3400 cm$^{-1}$.

U.V. spectrum: $\lambda_{max.}^{EtOH}$ 221, 253, 318, 376 nm.

EXAMPLE 10

3-Amino-4-piperidino-benzophenone 9.30 g. of 3-nitro-4-piperidino-benzophenone are reduced as described in Examples 1 or 2, and the crude product is crystallized from isopropanol. 7.6 g. of 3-amino-4-piperidino-benzophenone are obtained; m.p.: 99°–100° C.

| Analysis for $C_{18}H_{20}N_2O$: | | |
|---|---|---|
| Calculated: C 77.11 % | H 7.19 % | N 9.99 % |
| Found: C 77.20 % | H 7.31 % | N 10.05 % |

I.R. spectrum characteristic bands appear at 705, 730, 800, 865, 1645, 2805, 2860, 2940, 2960, 3350, and 3440 cm$^{-1}$.

U.V. spectrum: $\lambda_{max.}^{EtOH}$ 219, 252, 308, 362 nm.

EXAMPLE 11

3-Amino-4-piperidino-benzophenone

A mixture of 2.5 g. of 3-nitro-4-piperidino-benzophenone, 10 ml. of tetrahydrofuran, 2.5 ml. of cyclohexene and 20 mg. of metallic palladium is refluxed for 16 hours. The catalyst is filtered off, and the filtrate is evaporated to dryness under reduced pressure. The crude product is recrystallized from isopropanol to yield 1.82 g. of 3-amino-4-piperidino-benzophenone. The physical constants of the product are the same as listed in Example 10.

EXAMPLE 12

3-Amino-4-piperidino-benzophenone

A solution of 6.5 g. of 3-nitro-4-piperidino-benzophenone in 80 ml. of glacial acetic acid is added dropwise into a well stirred mixture of 5.3 g. of iron powder and 25 ml. of glacial acetic acid. The reaction mixture is kept at 80° to 90° C for about 2 hours. During this period the reaction takes place completely. The heterogeneous reaction mixture is cooled, filtered, and the filtrate is evaporated under reduced pressure. The residue is dissolved in water and the solution is rendered alkaline. This mixture is extracted with benzene, the benzene solution is washed with water until neutral, dried over anhydrous magnesium sulphate, filtered through a column filled with silica gel, and evaporated under reduced pressure. This way 4.5 g. of a solid, crystalline substance are obtained. The physical constants of the product are the same as given in Example 10.

EXAMPLE 13

3-Amino-4-piperidino-benzophenone 0.25 g. of activated carbon are suspended in 10 ml. of ethanol with vigorous stirring, under nitrogen atmosphere, thereafter 0.5 ml. of a 0.2 molar palladium chloride solution are added. After 1 minute of intensive stirring, 1 ml. of concentrated hydrochloric acid is added to the heterogeneous reaction mixture. The ethanol solution containing the active catalyst is admixed with an ethanol solution of 1.55 g. of 3-nitro-4-piperidino-benzophenone, thereafter 3.7 ml. of a 1 molar ethanol solution of sodium borohydride are added dropwise to the mixture. When the reaction terminates (after 10 to 15 minutes) the catalyst is removed by filtration, and the ethanol filtrate is poured into an aqueous solution containing excessive amounts of sodium hydroxide. The aqueous phase is extracted with several portions of benzene. The benzene solution is dried over anhydrous potassium carbonate, filtered, and evaporated to dryness under reduced pressure. The residue is recrystallized to yield 0.98 g. of 3-amino-4-piperidino-benzophenone, the physical constants of which are identical with those listed in Example 10.

EXAMPLE 14

3-Amino-4-(N-methyl-piperazino)-benzophenone 9.75 g. of 3-nitro-4-(N-methyl-piperazino)-benzophenone are reduced as described in Examples 1 or 2. The crude product is recrystallized from isopropanol to obtain 8.1 g. of 3-amino-4-(N-methyl-piperazino)-benzophenone; m.p.: 123°–124° C.

| Analysis for $C_{18}H_{21}N_3O$: | | |
|---|---|---|
| Calculated: C 73.19 % | H 7.17 % | N 14.23 % |
| Found: C 73.21 % | H 7.30 % | N 14.15 % |

I.R. spectrum: characteristic bands appear at 705, 725, 795, 880, 1650, 2750, 2800, 2850, 2940, 3160, 3300, and 3400 cm$^{-1}$.

U.V. spectrum: $\lambda_{max.}^{EtOH}$ 216, 252, 300, 358 nm.

If the methanol solution of the free base is admixed with the methanol solution of fumaric acid, and the mixture is diluted with ether, the corresponding monofumarate salt separates. This salt melts at 185°–186° C.

Using an isopropanol solution of hydrchlolic acid, the hydrochloride of the product is prepared; m.p.: 186°–188° C.

EXAMPLE 15

3-Amino-4-(N-methyl-piperazino)-benzophenone ethobromide

A mixture of 29.5 g. of 3-amino-4-(N-methyl-piperazino)-benzophenone, 300 ml. of acetone and 64 g. of ethyl bromide is stirred and refluxed for 2 hours. The mixture is cooled and left to stand overnight. The separated crystals are filtered off, washed with acetone, and dried. 33 g. of 3-amino-4-(N-methyl-piperazino)-benzophenone ethobromide are obtained: m.p.: 226°–227° C.

EXAMPLE 16

3-(3,4,5-Trimethoxybenzoylamino)-4-morpholino-benzophenone 28 g. of 3-amino-4-morpholino-benzophenone are dissolved in 560 ml. of acetone, and 17 g. of solid sodium hydrocarbonate are added. A solution of 25.4 g. of 3,4,5-trimethoxybenzoyl chloride in 260 ml. of acetone are added dropwise to the solution at room temperature, under vigorous stirring. The temperature of the reaction mixture rises with about 6° to 10° C. After the addition the mixture is stirred for additional 30 minutes at room temperature, then poured into ice water. The separated product is filtered off, washed with water, dried, and crystallized from a mixture of acetone and ether. 37.5 g. of 3-(3,4,5-trimethoxybenzoylamino)-4-morpholino-benzophenone are obtained; m.p.: 171°–172° C.

|  | Analysis for $C_{27}H_{28}N_2O_6$: | | |
|---|---|---|---|
| Calculated: | C 68.05 % | H 5.92 % | N 5.88 % |
| Found: | C 68.11 % | H 6.10 % | N 5.92 % |

I.R. spectrum: characteristic bands appear at 705, 720, 800, 850, 870, 1135, 1540, 1650, 1670, and 3330 cm$^{-1}$.

U.V. spectrum: $\lambda_{max.}^{EtOH}$ 223, 264, 284 nm.

EXAMPLE 17

3-Propionylamino-4-morpholino-benzophenone HCl

A solution of 10.2 g. of propionyl chloride in 50 ml. of acetone is added dropwise, at room temperature to a stirred solution of 28 g. of 3-amino-4-morpholino-benzophenone in 560 ml. of acetone. After the addition the reaction mixture is stirred for additional 30 minutes at room temperature. The separated crystalline 3-pripionyl-amino-4-morpholino-benzophenone hydrochloride is filtered off, and washed with ether. 34 g. of the aimed compound are obtained; m.p.: 152°–153° C.

The hydrochloride is treated with sodium hydroxide to liberate the base.

|  | Analysis for $C_{20}H_{22}N_2O_3$: | | |
|---|---|---|---|
| Calculated: | C 70.98 % | H 6.55 % | N 8.28 % |
| Found: | C 80.01 % | H 6.66 % | N 8.19 % |

I.R. spectrum characteristic bands appear at 705, 730, 800, 880, 1530, 1660, 1690, and 3350 cm$^{-1}$.

U.V. spectrum: $\lambda_{max.}^{EtOH}$ 220, 254, 324 nm.

EXAMPLE 18

3-Palmitoylamino-4-morpholino-benzophenone

This compound is prepared from 2.8 g. of 3-amino-4-morpholino-benzophenone and 3.02 g. of palmitoyl chloride as described in Example 16. The product melts at 70.5°–71.5° C.

|  | Analysis for $C_{33}H_{48}N_2O_3$: | | |
|---|---|---|---|
| Calculated: | C 76.11 % | H 9.29 % | N 5.38 % |
| Found: | C 76.18 % | H 9.31 % | N 5.42 % |

I.R. spectrum: characteristic bands appear at 710, 730, 800, 830, 1550, 1650, 1700, 2860, 2930, and 3380 cm$^{-1}$.

U.V. spectrum: $\lambda_{max.}^{EtOH}$ 256, 324 nm.

What we claim is:

1. A compound of the formula:

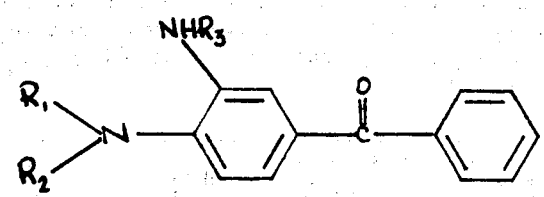

wherein $R_1$ and $R_2$ together with the adjacent nitrogen form a 5 or 6 member saturated heterocyclic which is interrupted only by the adjacent nitrogen, by an additional nitrogen or by oxygen; and is unsubstituted or substituted with a lower alkyl and $R_3$ is hydrogen or $C_1$ to $C_{18}$ acyclic acyl; or a pharmaceutically acceptable salt thereof.

2. 3-palmitoylamino-4-morpholino-benzophenone.
3. 3-Amino-4-morpholino-benzophenone hydrochloride.
4. 3-Amino-4-pyrrolidino-benzophenone.
5. 3-Amino-4-piperidino-benzophenone.
6. 3-Amino-4-(N-methyl-piperazino)-benzophenone.
7. 3-Amino-4-(N-methyl-piperazino)-benzophenone ethobromide.
8. 3-propionylamino-4-morpholino-benzophenone hydrochloride.

* * * * *